United States Patent
Song et al.

[11] Patent Number: 6,121,031
[45] Date of Patent: Sep. 19, 2000

[54] CYTOSOLIC PHOSPHOLIPASE $A_2$-GAMMA ENZYMES AND POLYNUCLEOTIDES ENCODING SAME

[75] Inventors: Chuanzheng Song, Brighton; Ronald Kriz, Hudson; John Knopf, Acton, all of Mass.

[73] Assignee: Genetics Institute, Inc., Cambridge, Mass.

[21] Appl. No.: 08/890,615

[22] Filed: Jul. 9, 1997

[51] Int. Cl.[7] .............. C12N 9/20; C12N 15/63; C12N 5/10; C07H 21/04

[52] U.S. Cl. .................. 435/198; 435/252.3; 435/320.1; 435/325; 536/23.2

[58] Field of Search ................ 435/198, 252.3, 435/320.1, 325; 536/23.2

[56] References Cited

U.S. PATENT DOCUMENTS

| | | | |
|---|---|---|---|
| 5,552,530 | 9/1996 | Johnson et al. | 530/387.9 |
| 5,554,511 | 9/1996 | Jones et al. | 435/69.1 |

*Primary Examiner*—Kawai Lau
*Attorney, Agent, or Firm*—Scott A. Brown

[57] ABSTRACT

The invention provides a novel calcium-independent cytosolic phospholipase $A_2$-Gamma enzyme, polynucleotides encoding such enzyme and methods for screening unknown compounds for anti-inflammatory activity mediated by the arachidonic acid cascade.

9 Claims, 4 Drawing Sheets

CYTOSOLIC PHOSPHOLIPASE A$_2$-GAMMA ENZYMES AND POLYNUCLEOTIDES ENCODING SAME

The present invention relates to a purified cytosolic phospholipase A$_2$-Gamma (cPLA$_2$-γ) enzymes which are useful for assaying chemical agents for anti-inflammatory activity.

BACKGROUND OF THE INVENTION

The phospholipase A$_2$ enzymes comprise a widely distributed family of enzymes which catalyze the hydrolysis of the acyl ester bond of glycerophospholipids at the sn-2 position. One kind of phospholipase A$_2$ enzymes, secreted phospholipase A$_2$ or sPLA$_2$, are involved in a number of biological functions, including phospholipid digestion, the toxic activities of numerous venoms, and potential antibacterial activities. A second kind of phospholipase A$_2$ enzymes, the intracellular phospholipase A$_2$ enzymes, also known as cytosolic phospholipase A$_2$ or cPLA$_2$, are active in membrane phospholipid turnover and in regulation of inflammation mediated by the multiple components of the well-known arachidonic acid cascade. One or more cPLA$_2$ enzymes are believed to be responsible for the rate limiting step in the arachidonic acid cascade, namely, release of arachidonic acid from membrane glycerophospholipids. The action of cPLA$_2$ also initiates the biosynthesis of platelet activating factor (PAF). U.S. Pat. Nos. 5,322,776, 5,354,677, 5,527,698 and 5,593,878 disclose such enzymes (sometimes referred to herein as "cPLA$_2$α").

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid cleavage of the sn-1 substituent, i.e., functionally equivalent to the combination of phospholipase A$_2$ and lysophospholipase (Saito et al., Methods of Enzymol., 1991, 197, 446; Gassama-Diagne et al., J. Biol. Chem., 1989, 264, 9470). Whether these two events occur at the same or two distinct active sites has not been resolved. It is also unknown if these enzymes have a preference for the removal of unsaturated fatty acids, in particular arachidonic acid, at the sn-2 position and accordingly contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. The efficacy of the present anti-inflammatory drugs which act through inhibition of arachidonic acid cascade steps is limited by the existence of side effects which may be harmful to various individuals.

A very large industrial effort has been made to identify additional anti-inflammatory drugs which inhibit the arachidonic acid cascade. In general, this industrial effort has employed the secreted phospholipase A$_2$ enzymes in inhibitor screening assays, for example, as disclosed in U.S. Pat. No. 4,917,826. However, because the secreted phospholipase A$_2$ enzymes are extracellular proteins (i.e., not cytosolic) and do not selectively hydrolyze arachidonic acid, they are presently not widely believed to contribute to prostaglandin and leukotriene production. While some inhibitors of the small secreted phospholipase A$_2$ enzymes have been reported to display anti-inflammatory activity, such as bromphenacyl bromide, mepacrine, and certain butyrophenones as disclosed in U.S. Pat. No. 4,239,780. The site of action of these compounds is unclear as these agents retain anti-inflammatory activity in mouse strains lacking sPLA$_2$. It is presently believed that inhibitor screening assays should employ cytosolic phospholipase A$_2$ enzymes which initiate the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase A$_2$ was identified, isolated, and cloned. Use of the cytosolic form of phospholipase A$_2$ to screen for anti-inflammatory drugs provides a significant improvement in identifying inhibitors of the arachidonic acid cascade. The cytosolic phospholipase A$_2$ disclosed in U.S. Pat. No. 5,322,776 is a 110 kD protein which depends on the presence of elevated levels of calcium inside the cell for its activity. The cPLA$_2$ of U.S. Pat. No. 5,322,776 plays a pivotal role in the production of leukotrienes and prostaglandins initiated by the action of pro-inflammatory cytokines and calcium mobilizing agents. The cPLA$_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the cPLA$_2$ of U.S. Pat. No. 5,322,776, some cells contain calcium independent phospholipase A$_2$/B enzymes. For example, such enzymes have been identified in rat, rabbit, canine and human heart tissue (Gross, TCM, 1991, 2, 115; Zupan et al., J. Med. Chem., 1993, 36, 95; Hazen et al., J. Clin. Invest., 1993, 91, 2513; Lehman et al., J. Biol. Chem., 1993, 268, 20713; Zupan et al., J. Biol. Chem., 1992, 267, 8707; Hazen et al., J. Biol. Chem., 1991, 266, 14526; Loeb et al., J. Biol. Chem., 1986, 261, 10467; Wolf et al., J. Biol. Chem., 1985, 260, 7295; Hazen et al., Meth. Enzymol., 1991, 197, 400; Hazen et al., J. Biol. Chem., 1990, 265, 10622; Hazen et al., J. Biol. Chem., 1993, 268, 9892; Ford et al., J. Clin. Invest., 1991, 88, 331; Hazen et al., J. Biol. Chem., 1991, 266, 5629; Hazen et al., Circulation Res., 1992, 70, 486; Hazen et al., J. Biol. Chem., 1991, 266, 7227; Zupan et al., FEBS, 1991, 284, 27), as well as rat and human pancreatic islet cells (Ramanadham et al., Biochemistry, 1993, 32, 337; Gross et al., Biochemistry, 1993, 32, 327), in the macrophage-like cell line, P388D$_1$ (Ulevitch et al., J. Biol. Chem., 1988, 263, 3079; Ackermann et al., J. Biol. Chem., 1994, 269, 9227; Ross et al., Arch. Biochem. Biophys., 1985, 238, 247; Ackermann et al., FASEB Journal, 1993, 7(7), 1237), in various rat tissue cytosols (Nijssen et al., Biochim. Biophys. Acta, 1986, 876, 611; Pierik et al., Biochim. Biophys. Acta, 1988, 962, 345; Aarsman et al., J. Biol. Chem., 1989, 264, 10008), bovine brain (Ueda et al., Biochem. Biophys, Res. Comm., 1993, 195, 1272; Hirashima et al., J. Neurochem., 1992, 59, 708), in yeast (*Saccharomyces cerevisiae*) mitochondria (Yost et al., Biochem. International, 1991, 24, 199), hamster heart cytosol (Cao et al., J. Biol. Chem., 1987, 262, 16027), rabbit lung microsomes (Angle et al., Biochim. Biophys. Acta, 1988, 962, 234) and guinea pig intestinal brush-border membrane (Gassama-Diagne et al., J. Biol. Chem., 1989, 264, 9470). U.S. Pat. Nos. 5,466,595, 5,554,511 and 5,589,170 also disclose calcium independent cPLA$_2$/B enzymes (sometimes referred to herein as "iPLA$_2$").

Figure 1:
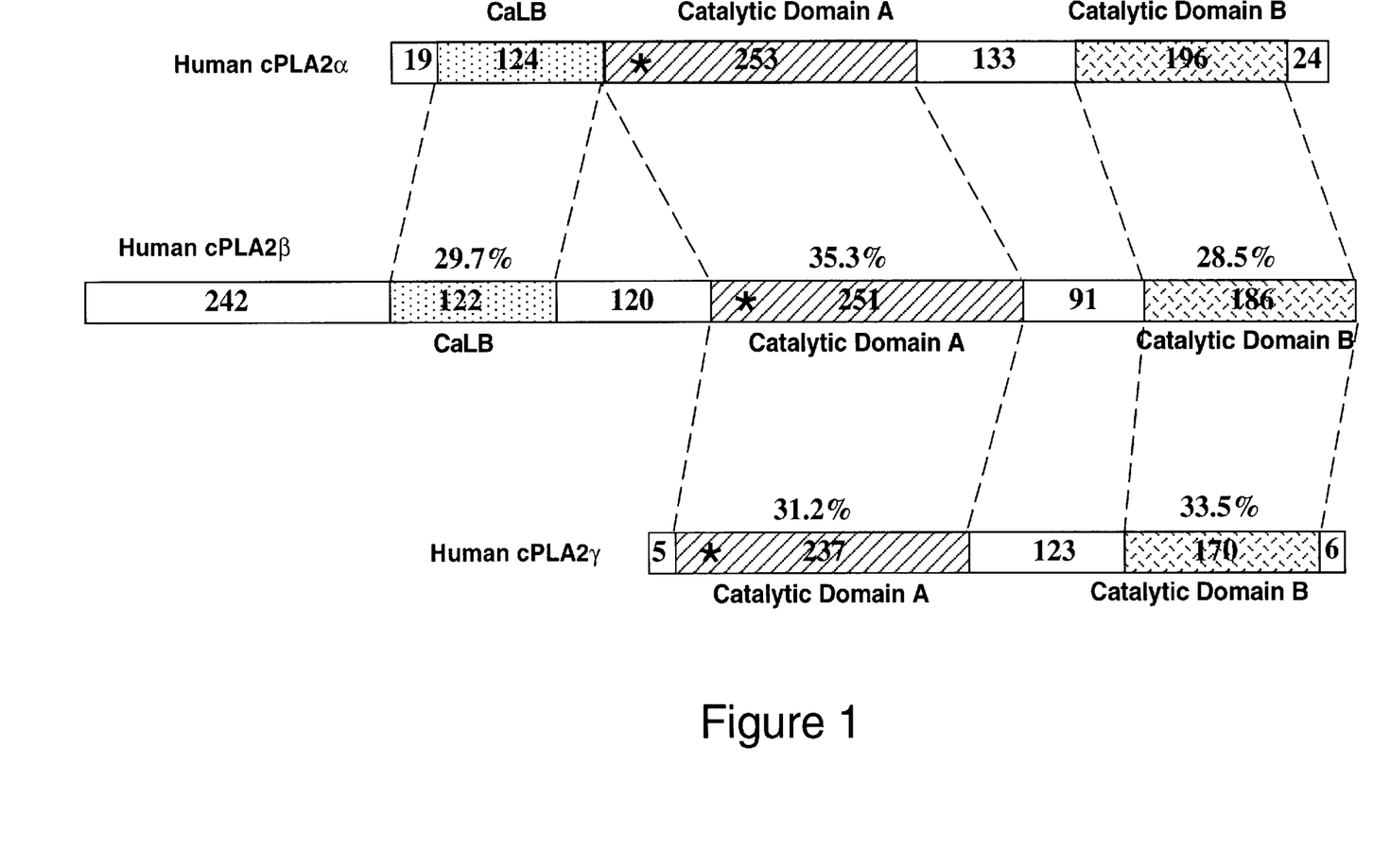

An additional cPLA$_2$, called "cPLA$_2\beta$", has also been identified. cPLA$_2\beta$ is described in co-pending application Ser. No. 08/788,975. Similar to cPLA$_2\alpha$, cPLA$_2\beta$ is a calcium dependent phospholipase with preference for arachidonic acid at the sn-2 position of the phospholips. Significant homology of amino sequences is found between the alpha and beta isoforms in three regions, namely the CaLB domain, catalytic domains A and B (see FIG. 1). This finding leads to the notion that cPLA$_2\alpha$ is a member of a multi-gene family and that more than one intracellular phospholipase A$_2$ might be involved in arachidonic acid release, mis regulation of which may lead to various human diseases including inflammation and cancer formation (Heasley et al., J. Biol. Chem. 1997, 272, 14501).

In addition, it is believed that the phospholipase enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the cPLA$_2$ of U.S. Pat. No. 5,322,776. In addition the activity may be more predominant in certain inflamed tissues over others.

Therefore, it would be desirable to identify and isolate additional cPLA$_2$ enzymes.

SUMMARY OF THE INVENTION

In other embodiments, the invention provides isolated polynucleotides comprising a nucleotide sequence selected from the group consisting of:

(a) the nucleotide sequence of SEQ ID NO: 1 from nucleotide 312 to nucleotide 1934;

(b) a nucleotide sequence encoding the amino acid sequence of SEQ ID NO: 2;

(c) a nucleotide sequence encoding a fragment of the amino acid sequence of SEQ ID NO: 2 having activity in a mixed micelle assay with 1-palmitoyl-2-[$^{14}$C]-arachidonyl-phosphatidylcholine;

(d) a nucleotide sequence capable of hybridizing with the sequence of (a), (b) or (c) which encodes a peptide having activity in a mixed micelle assay with 1-palmitoyl-2-[$^{14}$C]-arachidonyl-phosphatidylcholine;

(e) allelic variants of the sequence of (a); and (f) species homologues of the sequence of (a) or (b).

Expression vectors comprising such polynucleotides and host cells transformed with such vectors are also provided by the present invention. Compositions comprising peptides encoded by such polynucleotides are also provided.

The present invention also provides processes for producing a phospholipase enzyme, said process comprising: (a) establishing a culture of the host cell transformed with a cPLA$_2$-Gamma encoding polynucleotide in a suitable culture medium; and (b) isolating said enzyme from said culture. Compositions comprising a peptide made according to such processes are also provided.

Certain embodiments of the present invention provide compositions comprising a peptide comprising an amino acid sequence selected from the group consisting of:

(a) the amino acid sequence of SEQ ID NO: 2;

(b) a fragment of the amino acid sequence of SEQ ID NO: 2 having activity in a mixed micelle assay with 1-palmitoyl-2-[$^{14}$C]-arachidonyl-phosphatidylcholine; and (c) species homologues of (a);

such peptide being substantially free of other mammalian proteins.

The present invention also provides methods for identifying an inhibitor of phospholipase activity, said method comprising: (a) combining a phospholipid, a candidate inhibitor compound, and a composition comprising a phospholipase enzyme peptide; and (b) observing whether said phospholipase enzyme peptide cleaves said phospholipid and releases fatty acid thereby, wherein the peptide composition is one of those described above. Inhibitor of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

BRIEF DESCRIPTION OF THE FIGURES

FIG. 1 is a schematic representation of three human cPLA2 isoforms. The conserved domains are shaded alike. The percentages above conserved domains in cPLA2$\beta$ and cPLA2$\gamma$ indicate the degree of amino acid sequence identity to the corresponding regions of cPLA2$\alpha$. The numbers reflect the length (in amino acids) of each segment. CaLB refers to Calcium-dependent Lipid Binding domain.

FIG. 2 shows the tissue distribution of human cPLA2$\gamma$ mRNA. $^{32}$P-labeled cPLA2$\gamma$ cDNA probe synthesized from the 900 bp EcoRI/Not I fragment from IMAGE consortium clone #258543 was used to hybridize blotted mRNA samples isolated from different human tissues. The blots were washed under high-stringency conditions and exposed to X-ray film.

DETAILED DESCRIPTION OF THE INVENTION

A cDNA encoding the cPLA$_2$-Gamma of the present invention was isolated as described in Example 1. The sequence of the isoalted cDNA is reported as SEQ ID NO: 1. The amino acid sequence encoded by such cDNA is SEQ ID NO: 2.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variations of the cDNA sequence as set forth in SEQ ID NO: 1, that is, naturally-occurring alternative forms of the cDNAs of SEQ ID NO: 1 which also encode phospholipase enzymes of the present invention.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≧50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≧50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≧50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≧50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≧50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≧50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≧50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≧50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1xSSPE is 0.15M NaCl, 10mM $NaH_2PO_4$, and 1.25mM EDTA, pH 7.4) can be substituted for SSC (1xSSC is 0.15M NaCl and 15mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1xSSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3–6.4, incorporated herein by reference.

Preferably, each such hybridizing polynucleotide has a length that is at least 25%(more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the phospholipase enzyme peptides recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the phospholipase enzyme peptide is expressed by a host cell which has been transformed (transfected) with the ligated polynucleotide/expression control sequence.

A number of types of cells may act as suitable host cells for expression of the phospholipase enzyme peptide. Suitable host cells are capable of attaching carbohydrate side chains characteristic of functional phospholipase enzyme peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The phospholipase enzyme peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the phospholipase enzyme peptide n lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the phospholipase enzyme peptide is made in yeast or bacteria, it is necessary to attach the appropriate carbohydrates to the appropriate sites on the protein moiety covalently, in order to obtain the glycosylated phospholipase enzyme peptide. Such covalent attachments may be accomplished using known chemical or enzymatic methods.

The phospholipase enzyme peptide of the invention may also be expressed as a product of transgenic animals, e.g., as a component of the milk of transgenic cows, goats, pigs, or sheep which are characterized by somatic or germ cells containing a polynucleotide encoding the phospholipase enzyme peptide.

The phospholipase enzyme peptide of the invention may be prepared by culturing transformed host cells under culture conditions necessary to express a phospholipase enzyme peptide of the present invention. The resulting expressed protein may then be purified from cell extracts as described in the examples below.

Alternatively, the phospholipase enzyme peptide of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the phospholipase enzyme peptide from cell extracts may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the phospholipase enzyme peptide. Some or all of the foregoing purification steps, in various combinations, can also be employed to provide a substantially homogeneous isolated recombinant protein. The phospholipase enzyme peptide thus purified is substantially free of other mammalian proteins and is defined in accordance with the present invention as "isolated phospholipase enzyme peptide".

The $cPLA_2$-Gamma of the present invention may be used to screen for compounds having anti-inflammatory activity mediated by the various components of the arachidonic acid cascade. Many assays for phospholipase activity are known and may be used with the phospholipase $A_2$-Gamma on the present invention to screen unknown compounds. For example, such an assay may be a mixed micelle assay as described in Example 2. Other known phospholipase activity assays include, without limitation, those disclosed in U.S. Pat. No. 5,322,776. These assays may be performed manually or may be automated or robotized for faster screening. Methods of automation and robotization are known to those skilled in the art.

In one possible screening assay, a first mixture is formed by combining a phospholipase enzyme peptide of the present invention with a phospholipid cleavable by such peptide, and the amount of hydrolysis in the first mixture ($B_0$) is measured. A second mixture is also formed by combining the peptide, the phospholipid and the compound or agent to be screened, and the amount of hydrolysis in the second mixture (B) is measured. The amounts of hydrolysis in the first and second mixtures are compared, for example, by performing a $B/B_0$ calculation. A compound or agent is considered to be capable of inhibiting phospholipase activity (i.e., providing anti-inflammatory activity) if a decrease in hydrolysis in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the cPLA$_2$-Gamma of the present invention are in the development of monoclonal and polyclonal antibodies. Such antibodies may be generated by employing purified forms of the cPLA$_2$ or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study phospholipase A$_2$ activity and inflammatory conditions.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor (such as, for example, Alzheimer's disease). Pharmaceutical compositions of the invention comprise a therapeutically effective amount of a cPLA$_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 pg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration is preferably oral, but other known methods of administration for anti-inflammatory agents may be used. Administration of the anti-inflammatory compounds identified by the method of the invention can be carried out in a variety of conventional ways. For example, for topical administration, the anti-inflammatory compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the anti-inflammatory compound, about 2 to about 5% W/W of a gelling agent. The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B. F. Goodrich), hydroxypropyl methylcellulose phthalates such as Methocel (K100M premium; Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mM phosphate buffer, pH 7.5.

Cutaneous or subcutaneous injection may also be employed and in that case the anti-inflammatory compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the anti-inflammatory compound of the invention will be in the form of pyrogen-free, parenterally acceptable aqueous solutions. A preferred pharmaceutical composition for intravenous injection should contain, in addition to the anti-inflammatory compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

The amount of anti-inflammatory compound in the pharmaceutical composition of the present invention will depend upon the nature and severity of the condition being treated, and on the nature of prior treatments which the patient has undergone. Ultimately, the attending physician will decide the amount of anti-inflammatory compound with which to treat each individual patient.

Anti-inflammatory compounds identified using the method of the present invention may be administered alone or in combination with other anti-inflammation agents and therapies.

EXAMPLE 1

Clone Identification

Two cPLA$_2\gamma$-specific deoxyribonucleotides were designed based on the sequence of human EST clone #258543 (GenBank accession N56796), which was identified to be homologous to cPLA2$\alpha$ and cPLA2$\beta$ by searching the GenBank EST database using the amino acid sequence of cPLA2$\beta$ as a query:

| | |
|---|---|
| 5'-TTCGACTTCAGTGCCGGAGATCCT-3' | (SEQ ID NO: 3) |
| 5'-GGGAAAATGCATCACCACTGGTCC-3' | (SEQ ID NO: 4) |

Figure 2:
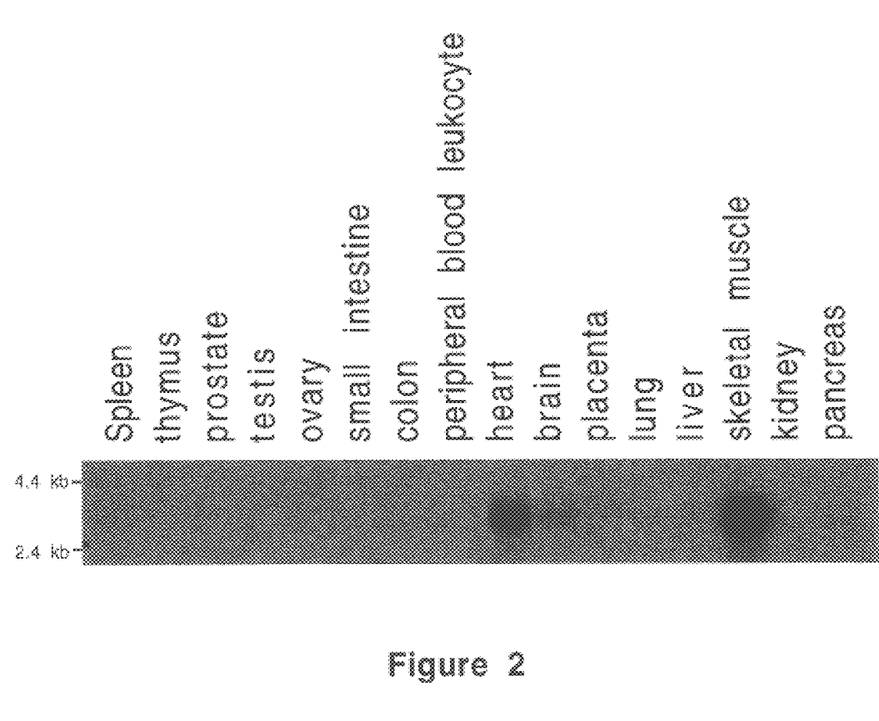
Figure 3:
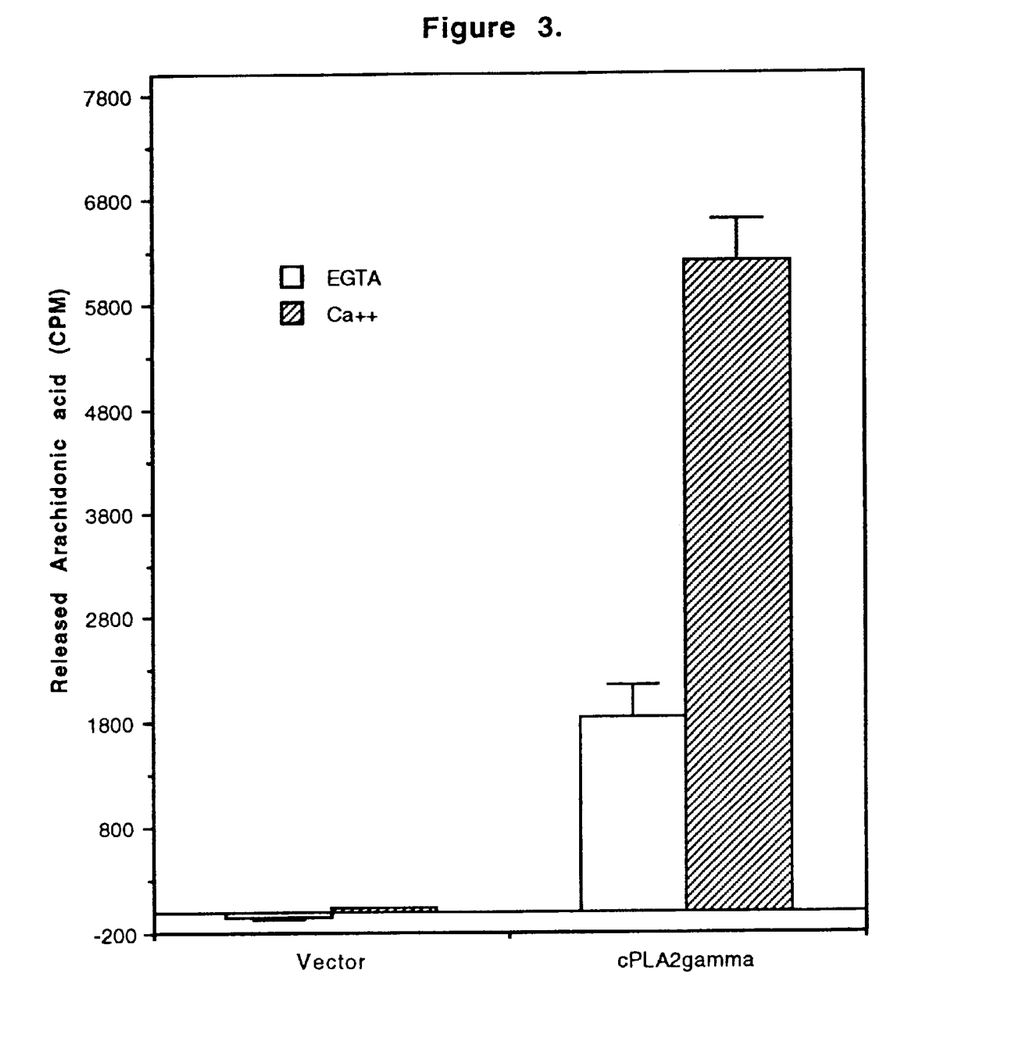
FIG. 3 presents data relating to the phospholipase A2 activity of lysates from COS-1 cells transfected with pED$\Delta$C (vector) or pED$\Delta$C-cPLA$_2\gamma$WT#53 (cPLA2gamma). Forty ul of the lysate was mixed on ice with 100 ul substrate containing 20 uM 1-palmitoyl-2-[1–14C]-arachidonyl-L-3-Phosphatidylcholine, 100 mM Tris-Ci, pH 7.5, 50 uM Triton-X 100, 10% glycerol and 5 mM EGTA. The reaction was carried out at 37° C. for 30 min and the products analyzed as described (PNAS 87, pp7708–7712, 1990). In the reactions with calcium (Ca++), CaCl$_2$ was added to a final concentration of 12.8 mM.
Figure 4:
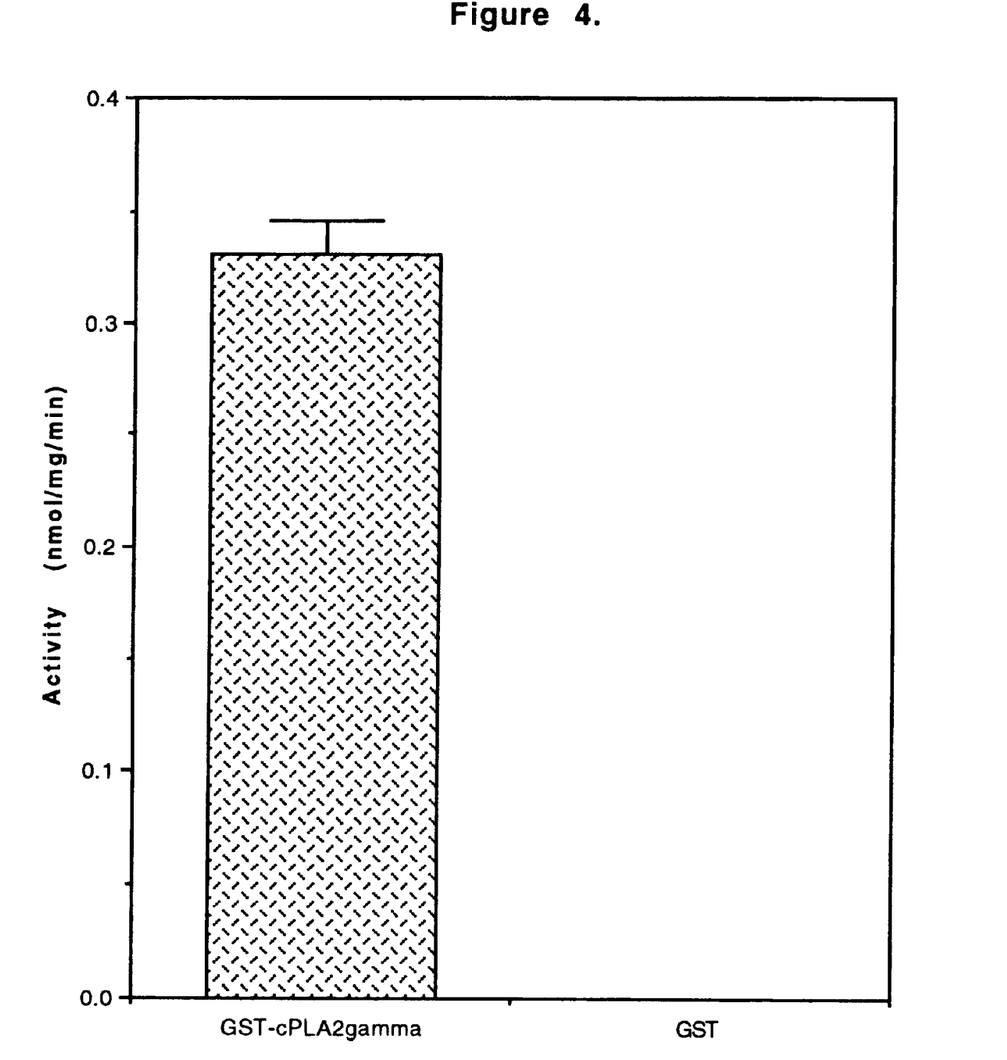
FIG. 4 presents data relating to the hydrolysis of lyso-PC substrate by E. coli expressed GST-cPLA2$\gamma$ fusion protein. Forty ul of the purified proteins (GST or GST-cPLA2$\gamma$) was mixed with 100 ul reaction buffer containing 80 mM HEPES, pH 7.5, 1 mM EGTA, 0.1 mg/ml of BSA and 4 uM L-1-(palmitoyl-1-$^{14}$C) phosphatidylcholine. The reactions were carried out at 37° C. for 30 min and the products analyzed as described (PNAS 87, pp7708–7712, 1990).

These oligo nucleotides were used to hybridize to the plasmid DNA isolated from IMAGE consortium clone #258543 to confirm its sequence. The 900 bp EcoRI/Not I fragment from clone #258543 was then used to probe human tissue northern blots purchased from Clontech (catalog #7759-1 and 7760-1) under high stringency hybridization conditions (See FIG. 2). A high level of expression for this gene was noted for human heart and skeletal muscle. The same probe fragment was then used to screen 10$^6$ recombinates of the oligo dT primed human skeletal muscle library purchased from Strategene (catalog #937209). Clone 19A. which is a phagemid DNA excised from the Lamda Uni-Zap XR phage vector, was examined for complete DNA sequence determination (SEQ ID NO: 1). The coding sequence on this clone begins at nucleotide 312 and continues to a stop codon at nucleotide 1935, representing 541 amino acids (see SEQ ID NO: 2).

A comparison of the cPLA$_2\gamma$ amino acid sequence with the sequences of cPLA$_2\alpha$ and cPLA$_2\beta$ reveals 28.7% and 29.6% overall identity, respectively. Mutiple sequence alignment of the amino acid sequences of the three cPLA2 isoforms also reveals that cPLA$_2\gamma$ lacks the calcium-dependent lipid binding (CaLB) domain found in the other two isoforms and that homology can be found in two subdomains in the catalytic region, namely, the catalytic domains A and B (See FIG. 1). The N-terminus of the encoded polypeptide begins with MGSS, which is a potential site for N-terminal myristoylation, and the C-terminus ends with CCLA, which is a potential site for double geranylgeranylation modification at the two consecutive cystidines.

Clone 19A was deposited with the American Type Culture Collection on Jun. 18, 1997 as accession number ATCC 98467.

Construction of Expression Vectors to Produce cPLA2$\gamma$ Protein in COS-7 Cells:

Two oligonucleotides were designed as follows:
Oligonucleotide A2GFWD:

| | |
|---|---|
| 5'-GTTCACCTCATCCTCTCCTTCGAC-3' | (SEQ ID NO: 5) |

Oligonucleotide A2GCWT:

| | |
|---|---|
| 5'-TCGGGGTACCGAATTCGGGCCCTATGC-CAAGCAGCAACTTCGGGCACT-3' | (SEQ ID NO: 6). |

These two oligonucleotides were used to amplify the 3'-end coding region of cPLA$_2\gamma$ using clone 19A DNA as template in a PCR reaction. The PCR product was digested with Xba I and Eco RI and the smaller DNA fragment was gel-purified and ligated with the XbaI/EcoRI fragment of clone 19A and EcoRI-digested vector pED$\Delta$C. The resulted clone, named pED$\Delta$C-cPLA$_2\gamma$WT#53 was confirmed to contain the desired C-terminal coding sequence by restriction enzyme digestion and DNA sequencing.

Transfection and Activity Assay:

Eight micrograms of plasmid pED$\Delta$C-cPLA$_2\gamma$WT#53 was transfected into COS-7 cells on a 10 cm cell culture plate using lipofectamine (GIBCO BRL) according to manufacturer's protocol. pED$\Delta$C vector DNA, pEMC-cPLA2 were also transfected in parallel experiments. At 33 hours posttransfection, cells were washed twice with 10 ml of ice-cold TBS, scraped into 1 ml of TBS. Cell pellets were collected, resuspended in lysis buffer (10 mM HEPES, pH 7.5, 1 mM EDTA, 0.1 mM DTT, 0.34 M sucrose, 1 mM PMSF and 1 $\mu$g/ml leupeptin) and lysed in a Parr-bomb (700 psi, 10 min) on ice. The lysate were centrifuged at 100,000 g for 0.5 hr at 4° C. The supernatant (cytosolic fraction) was transferred to another set of tubes and the pellets were resuspended in 0.5 volume of lysis buffer (particulate fraction).

Forty ul of the lysate was mixed on ice with 100 ul substrate containing 20 uM 1-palmitoyl-2-[1–14C]-arachidonyl-L-3-Phosphotidylcholine, 100 mM Tris-Cl, pH 7.5, 50 uM Triton-X 100, 10% glycerol and 5 mM EGTA. The reaction was carried out at 37° C. for 30 min and the products analyzed as described (PNAS 87, pp7708–7712, 1990).

Expression and Purification of cPLA$_2\gamma$ in *E. coli* as a GST Fusion Protein and Activity Assay:

The cPLA$_2\gamma$ gene was first subcloned into the plasmid pSE380 which places additional restriction sites at the 3' end of the gene, permitting facile subcloning into a GST fusion vector pGEX. The insert from cPLA$_2\gamma$ clone 19A was excised as an NcoI/KpnI fragment, starting at bp 311 and ending at the KpnI site located in the Bluescript polylinker region. This fragment was ligated into the vector pSE380 predigested with NcoI/KpnI, resulting in plasmid cPLA$_2\gamma$ clone 19A/pSE380. A NcoI/NotI fragment was excised from this plasmid and ligated with the following NcoI-to-BamHI converter into the BamHI/NotI cut pGEX-5X-3 GST fusion vector (Pharmacia).

| | |
|---|---|
| 5'-GATCGGTAGCGGTAGCAC-3' | (SEQ ID NO: 7) |
| 3'-CCATCGCCATCGTGGTAC-5' | (SEQ ID NO: 8) |
| GIGSGSTM | (SEQ ID NO: 9) |

The resulting construct, clone B1, produces a GST/cPLA$_2$-gamma fusion plasmid containing the complete coding sequence of cPLA$_2\gamma$ fused c-terminally to GST with a Gly-Ser-Gly-Ser spacer peptide.

Expression of the GST protein and GST-cPLA$_2\gamma$ fusion protein was induced with 0.3 mM IPTG at 37° C. for 3 hours after cells reached an O.D.$_{600}$ of 1.5. Cell pellets from 1 liter of culture were then harvested, resuspended in 30 ml of TBS containing 10% glycerol and various protease inhibitors and lysed in a Parr-bomb at 1500 PSI for 30 min. After treatment with DNase I and RNase A, cell lysate was centrifuged at 15000 rpm in a Sorvall SS34 rotor and the supernatant was mixed with 50% of glutathione Sepharose slury. After incubation at 4° C. for 1 hour, the glutathione beads were collected by centrifugation at 800 g and washed three times with 50 ml of lysis buffer. Bound protein was eluted in 2 ml of freshly prepared elution buffer (50 mM Tris-Cl, pH 8, 150 mM NaCl, 10% Glycerol, 5 mM EGTA, 1 mM DTT, 20 mM reduced glutathione). Forty ul of the eluted proteins was mixed with 100 ul reaction buffer containing 80 mM HEPES, pH 7.5, 1 mM EGTA, 0.1 mg/ml of BSA and 4 uM L-l-(palmitoyl-1-$^{14}$C) phosphatidylcholine. The reactions were carried out at 37° C. for 30 min and the products analyzed as described (PNAS 87, pp7708–7712, 1990).

EXAMPLE 2

Phopholipase Assays 1. sn-2 Hydrolysis Assays

A) Liposome: The lipid, e.g. 1-palmitoyl-2-[$^{14}$C] arachidonyl-sn-glycero-3-phosphocholine (PAPC), 55 mCi/mmol, was dried under a stream of nitrogen and solubilized in ethanol. The assay buffer contained 100 mM Tris-HCl pH 7, 4 mM EDTA, 4 mM EGTA, 10% glycerol and 25 μM of labelled PAPC, where the volume of ethanol added was no more than 10% of the final assay volume. The reaction was incubated for 30 minutes at 37° C. and quenched by the addition of two volumes of heptane:isopropanol:0.5M sulfuric acid (105:20:1 v/v). Half of the organic was applied to a disposable silica gel column in a vacuum manifold positioned over a scintillation vial, and the free arachidonic was eluted by the addition of ethyl ether (1 ml). The level of radioactivity was measured by liquid scintillation.

Variations on this assay replace EDTA and EGTA with 10 mM $CaCl_2$.

B) Mixed Micelle Basic: The lipid was dried down as in (A) and to this was added the assay buffer consisting of 80 mM glycine pH 9, 5 mM $CaCl_2$ or 5 mM EDTA, 10% or 70% glycerol and 200 μM triton X-100. The mixture was then sonicated for 30–60 seconds at 4° C. to form mixed micelles.

C) Mixed Micelle Neutral: As for (B) except 100 mM Tris-HCl pH 7 was used instead of glycine as the buffer.

2. sn-1 Hydrolysis Assays

Sn-1 hydrolysis assays are performed as described above for sn-1 hydrolysis, but using phospholipids labelled at the sn-1 substituent, e.g. 1-[$^{14}$C]-palmitoyl-2-arachidonyl-sn-glycero-3-phophocholine.

Patent and literature references cited herein are incorporated by reference as if fully set forth.

What is claimed is:

1. An isolated polynucleotide comprising a nucleotide sequence selected from the group consisting of:
   (a) the nucleotide sequence of SEQ ID NO: 1 from nucleotide 312 to nucleotide 1934;
   (b) a nucleotide sequence encoding the amino acid sequence of SEQ ID NO: 2;
   (c) a nucleotide sequence encoding a fragment of the amino acid sequence of SEQ ID NO: 2 having enzymatic activity in a mixed micelle assay with 1-palmitoyl-2-[$^{14}$C]-arachidonyl-phosphatidylcholine;
   (d) a nucleotide sequence capable of hybridizing under stringent conditions with the sequence of (a), (b) or (c) which encodes a peptide having enzymatic activity in a mixed micelle assay with 1-palmitoyl-2-[$^{14}$C]-arachidonyl-phosphatidylcholine;
   (e) allelic variants of the sequence of (a); and
   (f) species homologues of the sequence of (a) or (b).

2. An expression vector comprising the polynucleotide of claim 1 and an expression control sequence.

3. A host cell transformed with the vector of claim 2.

4. A process for producing a phospholipase enzyme, said process comprising:
   (a) establishing a culture of the host cell of claim 3 in a suitable culture medium; and
   (b) isolating said enzyme from said culture.

5. The polynucleotide of claim 1 comprising the nucleotide sequence of SEQ ID NO: 1 from nucleotide 312 to nucleotide 1934.

6. The polynucleotide of claim 1 comprising a nucleotide sequence encoding the amino acid sequence of SEQ ID NO: 2.

7. The polynucleotide of claim 6 wherein said polynucleotide comprises a nucleotide sequence which encodes the amino acid sequence of SEQ ID NO: 2 from amino acid 6 to amino acid 242.

8. The polynucleotide of claim 6 wherein said polynucleotide comprises a nucleotide sequence which encodes the amino acid sequence of SEQ ID NO: 2 from amino acid 366 to amino acid 535.

9. The polynucleotide of claim 1 comprising a nucleotide sequence encoding a fragment of the amino acid sequence of SEQ ID NO: 2 having enzymatic activity in a mixed micelle assay with 1-palmitoyl-2-[$^{14}$C]-arachidonyl-phosphatidylcholine.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 2454 base pairs
      (B) TYPE: nucleic acid
      (C) STRANDEDNESS: double
      (D) TOPOLOGY: linear    (ii) MOLECULE TYPE: cDNA    (iii) HYPOTHETICAL: NO    (ix) FEATURE:
      (A) NAME/KEY: CDS
      (B) LOCATION: 312..1934

(xi) SEQUENCE DESCRIPTION: SEQ ID NO:1:

```
GGCACGAGGC AGGGGCCATT TTACCTCCAG GTTGGCCCTG CTCAGGACCA GGAGGAAACA      60

CCTCCAGCCC GCGACCTCCT CCCACAGGGG GAAAAGGAAA GCAGGAGGAC CACAGAAGCT     120

TTGGCACCGA GGATCCCCGC AGTCTTCACC CGCGGAGATT CCGGCTGAAG GAGCTGTCCA     180

GCGACTACAC CGCTAAGCGC AGGGAGCCCA AGCCTCCGCA CCGGATTCCG GAGCACAAGC     240

TCCACCGCGC ATGCGCACAC GCCCCAGACC CAGGCTCAGG AGGACTGAGA ATTTTCTGAC     300

CGCAGTGCAC CATGGGAAGC TCTGAAGTTT CCATAATTCC TGGGCTCCAG AAAGAAGAAA     360

AGGCGGCCGT GGAGAGACGA AGACTTCATG TGCTGAAAGC TCTGAAGAAG CTAAGGATTG     420

AGGCTGATGA GGCCCCAGTT GTTGCTGTGC TGGGCTCAGG CGGAGGACTG CGGGCTCACA     480

TTGCCTGCCT TGGGGTCCTG AGTGAGATGA AGAACAGGG CCTGTTGGAT GCCGTCACGT      540

ACCTCGCAGG GGTCTCTGGA TCCACTTGGG CAATATCTTC TCTCTACACC AATGATGGTG     600

ACATGGAAGC TCTCGAGGCT GACCTGAAAC ATCGATTTAC CCGACAGGAG TGGGACTTGG     660

CTAAGAGCCT ACAGAAAACC ATCCAAGCAG CGAGGTCTGA GAATTACTCT CTGACCGACT     720

TCTGGGCCTA CATGGTTATC TCTAAGCAAA CCAGAGAACT GCCGGAGTCT CATTTGTCCA     780

ATATGAAGAA GCCCGTGGAA GAAGGGACAC TACCCTACCC AATATTTGCA GCCATTGACA     840

ATGACCTGCA ACCTTCCTGG CAGGAGGCAA GAGCACCAGA GACCTGGTTC GAGTTCACCC     900

CTCACCACGC TGGCTTCTCT GCACTGGGGG CCTTTGTTTC CATAACCCAC TTCGGAAGCA     960
```

-continued

```
AATTCAAGAA GGGAAGACTG GTCAGAACTC ACCCTGAGAG AGACCTGACT TTCCTGAGAG      1020

GTTTATGGGG AAGTGCTCTT GGTAACACTG AAGTCATTAG GGAATACATT TTTGACCAGT      1080

TAAGGAATCT GACCCTGAAA GGTTTATGGA GAAGGGCTGT TGCTAATGCT AAAAGCATTG      1140

GACACCTTAT TTTTGCCCGA TTACTGAGGC TGCAAGAAAG TTCACAAGGG AACATCCTC       1200

CCCCAGAAGA TGAAGGCGGT GAGCCTGAAC ACACCTGGCT GACTGAGATG CTCGAGAATT      1260

GGACCAGGAC CTCCCTGGAA AAGCAGGAGC AGCCCCATGA GGACCCCGAA AGGAAAGGCT      1320

CACTCAGTAA CTTGATGGAT TTTGTGAAGA AAACAGGCAT TTGCGCTTCA AAGTGGGAAT      1380

GGGGGACCAC TCACAACTTC CTGTACAAAC ACGGTGGCAT CCGGGACAAG ATAATGAGCA      1440

GCCGGAAGCA CCTCCACCTG GTGGATGCTG GTTTAGCCAT CAACACTCCC TTCCCACTCG      1500

TGCTGCCCCC GACGCGGGAG GTTCACCTCA TCCTCTCCTT CGACTTCAGT GCCGGAGATC      1560

CTTTCGAGAC CATCCGGGCT ACCACTGACT ACTGCCGCCG CCACAAGATC CCCTTTCCCC      1620

AAGTAGAAGA GGCTGAGCTG GATTTGTGGT CCAAGGCCCC CGCCAGCTGC TACATCCTGA      1680

AAGGAGAAAC TGGACCAGTG GTGATACATT TTCCCCTGTT CAACATAGAT GCCTGTGGAG      1740

GTGATATTGA GGCATGGAGT GACACATACG ACACATTCAA GCTTGCTGAC ACCTACACTC      1800

TAGATGTGGT GGTGCTACTC TTGGCATTAG CCAAGAAGAA TGTCAGGGAA ACAAGAAGA      1860

AGATCCTTAG AGAGTTGATG AACGTGGCCG GGCTCTACTA CCCGAAGGAT AGTGCCCGAA      1920

GTTGCTGCTT GGCATAGATG AGCCTCAGCT TCCAGGGCAC TGTGGGCCTG TTGGTCTACT      1980

AGGGCCCTGA AGTCCACCTG GCCTTCCTGT TCTTCACTCC CTTCAGCCAC ACGCTTCATG      2040

GCCTTGAGTT CACCTTGGCT GTCCTAACAG GGCCAATCAC CAGTGACCAG CTAGACTGTG      2100

ATTTTGATAG CGTCATTCAG AAGAAGGTGT CCAAGGAGCT GAAGGTGGTG AAATTTGTCC      2160

TGCAGGTCCC TCGGGAGATC CTGGAGCTGG AGCATGAGTG TCTGACAATC AGAAGCATCA      2220

TGTCCAATGT CCAGATGGCC AGAATGAATG TGATAGTTCA GACCAATGCC TTCCACTGCT      2280

CCTTTATGAC TGCACTTCTA GCCAGTAGCT CTGCACAAGT TAGCTCTGTA GAAGTAAGAA      2340

CTTGGGCTTA AATCATGGGC TATCTCTCCA CAGCCAAGTG GAGCTCTGAG AATACAACAA      2400

GTGCTCAATA AATGCTTGCT GATTGAAAAA AAAAAAAAAA AAAAAAAAAA AAAA          2454
```

(2) INFORMATION FOR SEQ ID NO:2:

(i) SEQUENCE CHARACTERISTICS:
        (A) LENGTH: 541 amino acids
        (B) TYPE: amino acid
        (C) STRANDEDNESS:
        (D) TOPOLOGY: linear     (ii) MOLECULE TYPE: protein     (ix) FEATURE:
        (A) NAME/KEY: Active-site
        (B) LOCATION: 6..242

(ix) FEATURE:
        (A) NAME/KEY: Active-site
        (B) LOCATION: 366..535

(xi) SEQUENCE DESCRIPTION: SEQ ID NO:2:

```
Met Gly Ser Ser Glu Val Ser Ile Ile Pro Gly Leu Gln Lys Glu Glu
 1               5                  10                  15

Lys Ala Ala Val Glu Arg Arg Arg Leu His Val Leu Lys Ala Leu Lys
                20                  25                  30

Lys Leu Arg Ile Glu Ala Asp Glu Ala Pro Val Val Ala Val Leu Gly
            35                  40                  45
```

```
Ser Gly Gly Gly Leu Arg Ala His Ile Ala Cys Leu Gly Val Leu Ser
 50                  55                  60
Glu Met Lys Glu Gln Gly Leu Leu Asp Ala Val Thr Tyr Leu Ala Gly
 65                  70                  75                  80
Val Ser Gly Ser Thr Trp Ala Ile Ser Ser Leu Tyr Thr Asn Asp Gly
                 85                  90                  95
Asp Met Glu Ala Leu Glu Ala Asp Leu Lys His Arg Phe Thr Arg Gln
                100                 105                 110
Glu Trp Asp Leu Ala Lys Ser Leu Gln Lys Thr Ile Gln Ala Ala Arg
            115                 120                 125
Ser Glu Asn Tyr Ser Leu Thr Asp Phe Trp Ala Tyr Met Val Ile Ser
130                 135                 140
Lys Gln Thr Arg Glu Leu Pro Glu Ser His Leu Ser Asn Met Lys Lys
145                 150                 155                 160
Pro Val Glu Glu Gly Thr Leu Pro Tyr Pro Ile Phe Ala Ala Ile Asp
                165                 170                 175
Asn Asp Leu Gln Pro Ser Trp Gln Glu Ala Arg Ala Pro Glu Thr Trp
            180                 185                 190
Phe Glu Phe Thr Pro His His Ala Gly Phe Ser Ala Leu Gly Ala Phe
            195                 200                 205
Val Ser Ile Thr His Phe Gly Ser Lys Phe Lys Lys Gly Arg Leu Val
210                 215                 220
Arg Thr His Pro Glu Arg Asp Leu Thr Phe Leu Arg Gly Leu Trp Gly
225                 230                 235                 240
Ser Ala Leu Gly Asn Thr Glu Val Ile Arg Glu Tyr Ile Phe Asp Gln
                245                 250                 255
Leu Arg Asn Leu Thr Leu Lys Gly Leu Trp Arg Arg Ala Val Ala Asn
            260                 265                 270
Ala Lys Ser Ile Gly His Leu Ile Phe Ala Arg Leu Leu Arg Leu Gln
            275                 280                 285
Glu Ser Ser Gln Gly Glu His Pro Pro Glu Asp Glu Gly Gly Glu
290                 295                 300
Pro Glu His Thr Trp Leu Thr Glu Met Leu Glu Asn Trp Thr Arg Thr
305                 310                 315                 320
Ser Leu Glu Lys Gln Glu Gln Pro His Glu Asp Pro Glu Arg Lys Gly
                325                 330                 335
Ser Leu Ser Asn Leu Met Asp Phe Val Lys Lys Thr Gly Ile Cys Ala
            340                 345                 350
Ser Lys Trp Glu Trp Gly Thr Thr His Asn Phe Leu Tyr Lys His Gly
            355                 360                 365
Gly Ile Arg Asp Lys Ile Met Ser Ser Arg Lys His Leu His Leu Val
370                 375                 380
Asp Ala Gly Leu Ala Ile Asn Thr Pro Phe Pro Leu Val Leu Pro Pro
385                 390                 395                 400
Thr Arg Glu Val His Leu Ile Leu Ser Phe Asp Phe Ser Ala Gly Asp
                405                 410                 415
Pro Phe Glu Thr Ile Arg Ala Thr Thr Asp Tyr Cys Arg Arg His Lys
            420                 425                 430
Ile Pro Phe Pro Gln Val Glu Glu Ala Glu Leu Asp Leu Trp Ser Lys
            435                 440                 445
Ala Pro Ala Ser Cys Tyr Ile Leu Lys Gly Glu Thr Gly Pro Val Val
450                 455                 460
```

```
Ile His Phe Pro Leu Phe Asn Ile Asp Ala Cys Gly Gly Asp Ile Glu
465                 470                 475                 480

Ala Trp Ser Asp Thr Tyr Asp Thr Phe Lys Leu Ala Asp Thr Tyr Thr
                485                 490                 495

Leu Asp Val Val Val Leu Leu Leu Ala Leu Ala Lys Lys Asn Val Arg
                500                 505                 510

Glu Asn Lys Lys Lys Ile Leu Arg Glu Leu Met Asn Val Ala Gly Leu
                515                 520                 525

Tyr Tyr Pro Lys Asp Ser Ala Arg Ser Cys Cys Leu Ala
                530                 535                 540

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:3:

TTCGACTTCA GTGCCGGAGA TCCT                                          24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

GGGAAAATGC ATCACCACTG GTCC                                          24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

GTTCACCTCA TCCTCTCCTT CGAC                                          24

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

TCGGGGTACC GAATTCGGGC CCTATGCCAA GCAGCAACTT CGGGCACT                 48
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:7:

GATCGGTAGC GGTAGCAC                                18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:8:

CATGGTGCTA CCGCTACC                                18

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS:
        (D) TOPOLOGY: linear     (ii) MOLECULE TYPE: peptide     (xi) SEQUENCE DESCRIPTION: SEQ ID NO:9:

Gly Ile Gly Ser Gly Ser Thr Met
1             5